United States Patent
Igarashi

(10) Patent No.: US 9,230,021 B2
(45) Date of Patent: Jan. 5, 2016

(54) IMAGE DIAGNOSTIC APPARATUS, IMAGE DIAGNOSTIC METHOD, MEDICAL IMAGE SERVER AND MEDICAL IMAGE STORAGE METHOD

(75) Inventor: Tsutomu Igarashi, Otawara (JP)

(73) Assignees: KABUSHIKI KAISHA TOSHIBA, Tokyo (JP); TOSHIBA MEDICAL SYSTEMS CORPORATION, Otawara-Shi, Tochigi (JP)

( * ) Notice: Subject to any disclaimer, the term of this patent is extended or adjusted under 35 U.S.C. 154(b) by 658 days.

(21) Appl. No.: 13/545,312

(22) Filed: Jul. 10, 2012

(65) Prior Publication Data
US 2012/0278359 A1    Nov. 1, 2012

Related U.S. Application Data

(63) Continuation of application No. PCT/JP2011/079561, filed on Dec. 20, 2011.

(30) Foreign Application Priority Data

Jan. 11, 2011  (JP) .................................... 2011-3506

(51) Int. Cl.
*G06F 17/30* (2006.01)
*G06F 19/00* (2011.01)
(Continued)

(52) U.S. Cl.
CPC ...... *G06F 17/30864* (2013.01); *G06F 17/3087* (2013.01); *G06F 19/321* (2013.01); *G06F 19/3406* (2013.01); *A61B 5/055* (2013.01); *A61B 8/12* (2013.01); *A61N 7/02* (2013.01)

(58) Field of Classification Search
CPC .......... G06F 17/3087; G06F 17/30997; G06F 17/30864; G06F 17/30867; H04L 67/12; H04L 67/38; A61N 7/02; A61B 8/12
USPC .......................................... 707/769; 600/439
See application file for complete search history.

(56) References Cited

U.S. PATENT DOCUMENTS

| 8,238,628 B2* | 8/2012 | Kazuno ................. G06F 19/321 382/128 |
| 8,386,273 B2 | 2/2013 | Kaminaga et al. |
| 8,510,031 B2* | 8/2013 | Williams .......... G06F 17/30864 707/705 |

(Continued)

FOREIGN PATENT DOCUMENTS

| CN | 101123911 A | 2/2008 |
| JP | 2003-58140 | 2/2003 |

(Continued)

OTHER PUBLICATIONS

Notification of Transmittal of Translation of the International Preliminary Report on Patentability in PCT/JP2011/079561 mailed Jul. 25, 2013.

(Continued)

*Primary Examiner* — Shahid Alam
(74) *Attorney, Agent, or Firm* — Nixon & Vanderhye P.C.

(57) ABSTRACT

An image diagnostic apparatus includes an examination information acquisition unit and an imaging unit. The examination information acquisition unit searches a medical image server based on patient information to acquire past examination information corresponding to the patient information automatically from the medical image server. The imaging unit performs imaging according to an imaging condition set by referring to the examination information. Alternatively, an image diagnostic apparatus includes an imaging condition setting unit and an imaging unit. The imaging condition setting unit automatically sets or indicates an imaging condition closest to information designating an imaging condition included in examination order information directed to an image diagnostic apparatus made by another maker or a different type of an image diagnostic apparatus made by a same maker. The imaging unit performs imaging according to the set or indicated imaging condition.

14 Claims, 3 Drawing Sheets

(51) Int. Cl.
*A61N 7/02* (2006.01)
*A61B 8/12* (2006.01)
*A61B 5/055* (2006.01)

(56) References Cited

U.S. PATENT DOCUMENTS

| | | | | |
|---|---|---|---|---|
| 2007/0282908 | A1* | 12/2007 | Van der Meulen | G06F 17/30997 707/802 |
| 2010/0160779 | A1* | 6/2010 | Browning | A61B 5/02007 600/439 |
| 2010/0160780 | A1* | 6/2010 | Swan | A61B 5/02007 600/439 |
| 2011/0161365 | A1* | 6/2011 | Shin | G06F 17/3087 707/769 |
| 2011/0306870 | A1* | 12/2011 | Kuhn | A61N 1/406 600/411 |

FOREIGN PATENT DOCUMENTS

| | | |
|---|---|---|
| JP | 2007-167634 | 7/2007 |
| JP | 2008-259707 | 10/2008 |
| JP | 2008-287653 | 11/2008 |
| JP | 2008-289855 | 12/2008 |
| JP | 2009-131614 | 6/2009 |
| JP | 2010-29284 | 2/2010 |
| JP | 2010-136824 | 6/2010 |
| JP | 2010-142462 | 7/2010 |
| JP | 2010-259614 | 11/2010 |
| JP | 2010-284175 | 12/2010 |

OTHER PUBLICATIONS

International Search Report for PCT/JP2011/079561 mailed Mar. 27, 2012 (in JP).

Written Opinion of the International Searching Authority mailed Mar. 27, 2012.

Office Action issued Feb. 4, 2015 in CN Patent Application No. 201180003316.0.

Office Action issued Jul. 17, 2015 in CN Patent Application No. 201180003316.0.

Office Action issued Aug. 10, 2015 in JP Patent Application No. 2011-278928.

* cited by examiner

| EXAMINATION ORDER | | PAST EXAMINATION INFORMATION | |
|---|---|---|---|
| ID: | XXX | EXAMINATION DATE: | XX/XX/XX |
| NAME: | XX XX | EXAMINATION TIME: | XX:XX |
| HEIGHT: | XX cm | DOCTOR'S NAME: | XX/XX/XX |
| WEIGHT: | XX kg | ENGINEER'S NAME: | XX/XX/XX |
| SEX: | XX | IMAGING PART: | XX |
| BIRTH DATE: | XX/XX/XX | PAS: | XX |
| AGE: | XX YEARS | | |
| IMAGING PART: | XX | | |

SE
2010/9/1 13:11
3×3×3
Filter: 2.0Hz 20.0×20.0×20.0mm
TR=1000.0
TE=136.0

PAS SETTING
PAS: XX

PATIENT REGISTRATION

PAS REGISTRATION

IMAGE DIAGNOSTIC APPARATUS, IMAGE DIAGNOSTIC METHOD, MEDICAL IMAGE SERVER AND MEDICAL IMAGE STORAGE METHOD

CROSS REFERENCE TO RELATED APPLICATION

This is a continuation of Application PCT/JP2011/079561, filed Dec. 20, 2011.

This application is based upon and claims the benefit of priority from Japanese Patent Application No. 2011-003506, filed Jan. 11, 2011; the entire contents of which are incorporated herein by reference.

FIELD

Embodiments described herein relate generally to an image diagnostic apparatus, an image diagnostic method, a medical image server and a medical image storage method.

BACKGROUND

Conventionally, for an image diagnostic apparatus such as MRI (Magnetic Resonance Imaging) apparatus, PAS (programmable anatomical system) information is generated as an imaging plan for each examination order. The PAS information consists of imaging parameters corresponding to each imaging part. Thus, an operator can preset an imaging protocol precedently to a scan by composing PAS information.

When PAS information is made, past examination information and images acquired in the past can be referred to. Patient attribute information, such as a name of patient, and an imaging part for each patient can be obtained as past examination order information through a network from a RIS (Radiology Information System). Further, past examination information can be also obtained by referring to medical records.

On the other hand, image data acquired by various types of modalities are stored in a PACS (picture archiving and communication system) as image data along the DICOM (Digital Imaging and Communication in Medicine) protocol. Accordingly, past examination images can be read from a PACS to an image diagnostic apparatus via a network. Therefore, for a reexamination of a same patient, an imaging plan can be made using past examination information obtained from a PACS.

PRIOR TECHNICAL LITERATURE

[Patent literature 1] JPA 2006-231040

However, works to search past examination information and input imaging parameters in an image diagnostic apparatus are required for setting an imaging plan. In addition, when medical records are referred to for setting same imaging conditions for a reexamination, works that an operator reads out imaging conditions from the medical records and inputs the imaging conditions in an image diagnostic apparatus is necessary.

Meanwhile, when no past examination exists or when an operator sets equivalent imaging positions with observing images in spite of existence of a past examination, it is a problem that setting imaging conditions depends on experience and skills of the operator.

It is an object of the present invention to provide an image diagnostic apparatus, an image diagnostic method, a medical image server and a medical image storage method which can set appropriate imaging conditions more easily.

BRIEF DESCRIPTION OF THE DRAWINGS

In the accompanying drawings:

FIG. 3 is a view showing an example of setting screen for imaging conditions in MRI in case of setting the imaging conditions based on both examination order information and past examination information in the imaging condition setting unit shown in FIG. 1.

DETAILED DESCRIPTION

Figure 1:
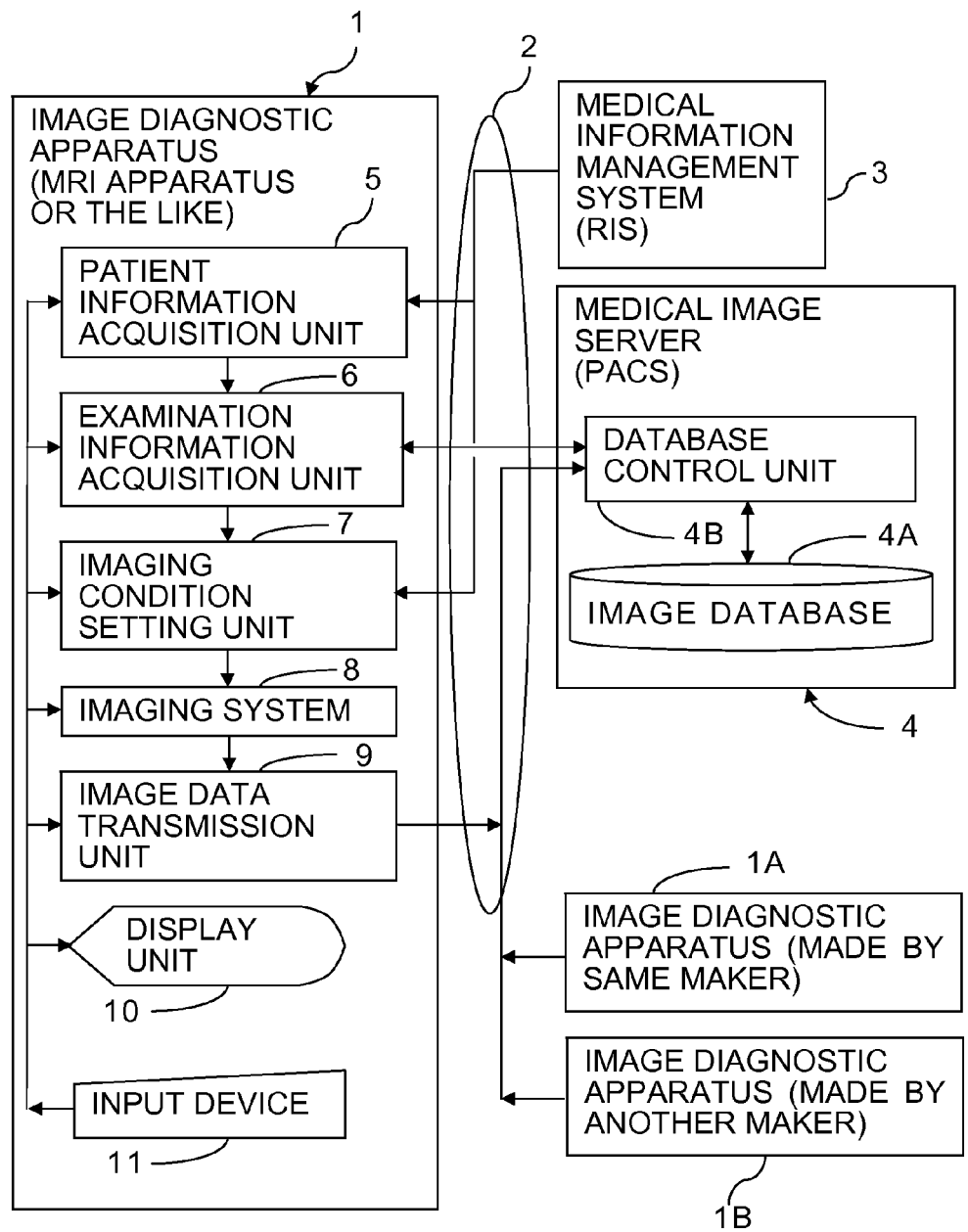
FIG. 1 is a functional block diagram of an image diagnostic apparatus and a medical image server according to an embodiment of the present invention.

According to one embodiment, an image diagnostic apparatus includes an examination information acquisition unit and an imaging unit. The examination information acquisition unit is configured to search a medical image server based on patient information to acquire past examination information corresponding to the patient information automatically from the medical image server when the patient information was supplied from a medical information management system. The imaging unit is configured to perform imaging according to an imaging condition set by referring to the examination information.

According to another embodiment, an image diagnostic apparatus includes an imaging condition setting unit and an imaging unit. The imaging condition setting unit is configured to automatically set or indicate an imaging condition closest to information designating an imaging condition included in examination order information directed to an image diagnostic apparatus made by another maker or a different type of an image diagnostic apparatus made by a same maker when the examination order information is supplied from a medical information management system. The imaging unit is configured to perform imaging according to the set or indicated imaging condition.

According to another embodiment, a medical image server includes a database and a database controlling unit. The database is configured to store medical image data. The database controlling unit is configured to search the database based on patient information managed in a medical information management system to acquire past examination information corresponding to the patient information to transmit the acquired past examination information to an image diagnostic apparatus when a request for transmitting the past examination information corresponding to the patient information was transmitted from the image diagnostic apparatus.

According to another embodiment, an image diagnostic method includes searching a medical image server based on patient information to acquire past examination information corresponding to the patient information automatically from the medical image server when the patient information was supplied from a medical information management system; and performing imaging according to an imaging condition set by referring to the examination information.

According to another embodiment, an image diagnostic method includes automatically setting or indicating an imaging condition closest to information designating an imaging condition included in examination order information directed to an image diagnostic apparatus made by another maker or a different type of an image diagnostic apparatus made by a same maker when the examination order information is supplied from a medical information management system; and performing imaging according to the set or indicated imaging condition.

According to another embodiment, a medical image storage method includes storing medical image data; and searching the medical image data based on patient information managed in a medical information management system to acquire past examination information corresponding to the patient information to transmit the acquired past examination information to an image diagnostic apparatus when a request for transmitting the past examination information corresponding to the patient information was transmitted from the image diagnostic apparatus.

An image diagnostic apparatus, an image diagnostic method, a medical image server and a medical image storage method according to an embodiment of the present invention will be described with reference to the accompanying drawings.

FIG. 1 is a functional block diagram of an image diagnostic apparatus and a medical image server according to an embodiment of the present invention;

The image diagnostic apparatus 1 is connected with a medical information management system 3 and a medical image server 4 through a network 2. In addition, another image diagnostic apparatus 1A made by the same maker and another image diagnostic apparatus 1B made by another maker may be connected with the network 2. As those in the art will appreciate, each of the diagnostic image apparatuses 1, 1A, 1B and the medical information management system 3 and the medical image server 4 includes at least one processor and associated memory configured by computer programs and/or hardware to effect their respective functionalities.

The medical information management system 3 is a system such as a RIS or a HIS (hospital information system) for managing examination order information of respective patients including patient information and information designating imaging conditions such as information specifying an imaging part. The patient information includes a body shape, a sex and an age of each patient.

The medical image server 4 is an image data management system such as a PACS which acquires and stores medical mage data along the DICOM protocol. The medical image server 4 has an image database 4A and a database control unit 4B. The database control unit 4B can be configured by a computer in which a control program has been installed. Alternatively, circuits may be used for configuring the database control unit 4B.

The image database 4A is a database to store medical image data. The medical image data is transmitted and received as image data along the DICOM protocol between the medical image server 4 and another device. Accordingly, the medical image data is stored as data classified according to information specifying patients, studies, series and images in the image database 4A. Therefore, attribute information to specify patients, studies, series and images to which respective frames of medical image data attribute may be stored for search aside from the medical image data in the image database 4A.

A type of medical image data along the DICOM protocol is classified and specified by a standard tag, a private tag and an image tag. The respective pieces of data classified by the standard tag and the private tag are information attached to medical image data along the DICOM protocol. Note that, information attached to medical image data along the DICOM protocol as tag information may be practically stored without attaching to the medical image data in the image database 4A.

That is, medical image data is transmitted and received as data along the DICOM protocol between the medical image server 4 and another medical device. However, the medical image data can be stored with an arbitrary data structure in the image database 4A. Therefore, incidental information of a frame of medical image data may be directly specified and acquired based on search conditions including attribute information specifying a patient, a study, a series and an image, to which the fame of the medical image data belongs, and data for search.

The database control unit 4B has a function to write and store medical image data, transmitted from a transmission source such as an image diagnostic apparatus 1, 1A or 1B via the network 2, in the image database 4A. The database control unit 4B also has a function to search the image database 4A based on searching conditions when a request of transmitting medical image data or study information corresponding to the medical image data have been transmitted with the searching conditions from the image diagnostic apparatus 1 via the network 2 to transmit medical image data along the DICOM protocol or study information corresponding to the medical image data, acquired as search results, to the image diagnostic apparatus 1.

The image diagnostic apparatus 1 includes a patient information acquisition unit 5, an examination information acquisition unit 6, an imaging condition setting unit 7, an imaging system 8, an image data transmission unit 9, an input device 10 and a display unit 11. The elements, performing processing of digital information, out of the patient information acquisition unit 5, the examination information acquisition unit 6, the imaging condition setting unit 7, the imaging system 8 and the image data transmission unit 9 can be configured by installing program with a computer. However, some circuits may be used for configuring those elements.

Examples of the image diagnostic apparatus 1 include an X-ray CT (computed tomography) apparatus, a nuclear medical diagnostic apparatus such as a PET (positron emission computed tomography) apparatus or a SPECT (single photon emission computed tomography) apparatus, an ultrasonic diagnostic apparatus and an X-ray diagnostic apparatus as well as a MRI apparatus. In each case, as those in the art will appreciate, patient anatomy to be imaged is positioned for imaging with respect to physical imaging apparatus that transmits electromagnetic radiation or ultra-sonic vibrations into the patient anatomy and, based on a sensed response, generates a diagnostic image representing the patient anatomy.

The patient information acquisition unit 5 has a function to acquire patient information included in examination order information for each patient and study when the examination order information has been supplied to the image diagnostic apparatus 1 from the medical information management system 3 through the network 2. The patient information acquired in the patient information acquisition unit 5 includes patient-specific information such as a name, an ID, a height, a weight, a sex, a date of birth and an age of a patient. Further, desired information, included in examination order information, such as information specifying an imaging part can be added to the patient information acquired by the patient information acquisition unit 5 as incidental information.

Note that, the patient information acquisition unit 5 is configured to be able to acquire patient information included in examination order information when not only examination order information directed to the image diagnostic apparatus 1 or 1A made by a same maker but also that directed to an image diagnostic apparatus 1B made by another maker has been supplied from the medical information management system 3.

The examination information acquisition unit 6 has a function to automatically transmit request of transmission of past examination information corresponding to patient information and search conditions of the examination information to the medical image server 4 through the network 2 when the patient information acquisition unit 5 has acquired the patient information and a function to receive and acquire the past examination information when the past examination information has been transmitted from the medical image server 4 as a response to the request of transmission of the past examination information. Therefore, operation of the examination information acquisition unit 6 makes it possible to search the medical image server 4 based on patient information to automatically acquire past examination information corresponding to the patient information, in the image diagnostic apparatus 1 side, from the medical image server 4 when the patient information was supplied from the medical information management system 3 to the image diagnostic apparatus 1.

Examination information to be a target of transmission request can be medical image data itself, examination information included in medical image data or examination information, corresponding to medical image data, stored separately from the medical image data. When medical image data is stored as DICOM image data in the medical image server 4, examination information can be acquired from tag information attached to the medical image data.

As described above, the DICOM image data includes pieces of data identified by an image tag, a standard tag and a private tag respectively. Medical image data itself is recorded in a data area identified by the image tag of the DICOM image data. Common data, such as imaging conditions and a patient ID, attached to medical image data and independent of a maker, a version, a grade and the like of an image diagnostic apparatus are recorded in a data area identified by the standard tag of DICOM image data. Furthermore, data, such as imaging conditions, attached to medical image data and specific to a maker, a version, a grade and the like of an image diagnostic apparatus is recorded in data area identified by the private tag of the DICOM image data.

Therefore, examination information such as imaging conditions corresponding to specific patient information can be acquired from the data areas identified by the standard tag and the private tag of DICOM image data. Meanwhile, medical image data can be acquired as examination information from the data area identified by the image tag.

On the other hand, when tag information having been attached to DICOM image data is stored in the medical image server 4 without attaching to the medical image data, examination information such as imaging conditions can be acquired by searching information corresponding to pieces of data identified by the standard tag and the private tag. Further, medical image data itself can be acquired as examination information by searching information corresponding to data identified by the image tag. In this case, information specifying a patient, a study, a series and an image can be used for searching conditions to perform a search.

Searching conditions of examination information can include arbitrary information, such as an imaging time and date, other than patient information besides information specifying a patient ID and the like included in patient information acquired by the patient information acquisition unit 5 and information specifying an imaging part. That is, the examination information acquisition unit 6 is configured to be able to require searching and transmitting past examination information, corresponding to attributions including a specific patient, imaging part and imaging time and date, to the medical image server 4 to acquire the past examination information. Therefore, the newest imaging time and date can be regarded as a searching condition of past examination information, for example. Alternatively, a threshold that an imaging time and date is within past three months or the like can be set as a searching condition, for example.

Note that, when no examination information of a patient specified by patient information is stored in the medical image server 4, past examination information of a patient having equivalent characteristics such as a body shape, a sex and an age may be acquired from the medical image server 4 by the examination information acquisition unit 6.

Thus, the database control unit 4B of the medical image server 4 is configured to search the image database 4A based on patient information managed in the medical information management system 3 to acquire examination information corresponding to the patient information to transmit the acquired examination information to the image diagnostic apparatus 1 when a request for transmitting past examination information corresponding to the patient information was transmitted from the image diagnostic apparatus 1. Herewith, the database control unit 4B can respond to the above mentioned function of the examination information acquisition unit 6.

The imaging condition setting unit 7 has a function to set imaging conditions based on examination order information supplied from the medical information management system 3 and instruction input from the input device 10. Especially, the imaging condition setting unit 7 is configured to set imaging conditions based on both examination order information and past examination information when the past examination information has been acquired by the examination information acquisition unit 6.

For example, if the image diagnostic apparatus 1 is a MRI apparatus, imaging conditions including a pulse sequence for MRI are set in the imaging condition setting unit 7. Approximately 100 imaging parameters including an echo time (TE), a repetition time (TR), data acquisition positions and a matrix size are required for setting a pulse sequence. On the other hand, if the image diagnostic apparatus 1 is an X-ray CT apparatus, imaging conditions including a gantry tilt angle, a bed position, a dose of X-ray exposed to an object and a data acquisition area are set by the imaging condition setting unit 7.

Setting imaging conditions can be also performed based on examination order information directed to not only the image diagnostic apparatus 1 or 1A made by the same maker but also the image diagnostic apparatus 1B made by another maker. Rough imaging conditions, which can be set in advance, such as an imaging part included as information designating imaging conditions in the examination order information can be set automatically as imaging conditions for imaging in the imaging condition setting unit 7. For example, when the imaging diagnostic apparatus 1 is a MRI apparatus, imaging conditions such as applications of an ECG synchronization and injection of contrast agent and a type of a reception coil of NMR signals can be set automatically based on information designating imaging conditions included in examination order information.

However, when examination order information directed to the image diagnostic apparatus 1B made by another maker or a different type of the image diagnostic apparatus 1A made by the same maker is supplied to the image diagnostic apparatus 1 from the medical information management system 3, information designating imaging conditions, such as a type of reception coil, included in the examination order information may not be an imaging condition which can be set in the image diagnostic apparatus 1.

Accordingly, the imaging condition setting unit 7 is configured to automatically set the closest imaging conditions to information designating imaging conditions included in examination order information directed to the image diagnostic apparatus 1B made by another maker or a different type of the image diagnostic apparatus 1A made by the same maker when the imaging condition setting unit 7 has acquired the examination order information. For example, a pulse sequence more consistent with information designating imaging conditions included in examination order information directed to a MRI apparatus made by another maker can be set as an imaging protocol for MRI based on the information designating imaging conditions by the imaging condition setting unit 7.

On the other hand, when past examination information has been acquired by the examination information acquisition unit 6, i.e., when the past examination information has been acquired by a search in the medical image server 4, imaging conditions can be automatically set based on more detailed information of imaging conditions included in the past examination information by the imaging condition setting unit 7.

When pieces of examination information corresponding to plural past examinations has been acquired, the imaging condition setting unit 7 is configured to be able to select past examination information acquired by imaging conditions matching with or closest to information designating imaging conditions such as an imaging part included in examination order information for setting imaging conditions. The imaging condition setting unit 7 can select past examination information for setting imaging conditions automatically based on information designating imaging conditions included in examination order information. Note that, the imaging condition setting unit 7 may display a list of examination information corresponding to plural past examinations on the display unit 11 so that an operator can select past examination information for setting imaging conditions manually by operating the input device 10.

The imaging condition setting unit 7 can automatically set detailed imaging conditions based on past examination information if all data required for setting imaging parameters consisting of imaging conditions are included in the past examination information. Especially, if the past examination information is medical image data along the DICOM protocol acquired by the same version and grade of the image diagnostic apparatus made by the same maker, the imaging condition setting unit 7 can automatically set all imaging parameters based on data corresponding to the standard tag and the private tag.

On the other hand, even if all data required for setting imaging conditions are not included in past examination information, partial imaging conditions can be set automatically based on data included in the examination information. For example, detailed imaging parameters including a TR and a TE of a pulse sequence can be set automatically by the imaging condition setting unit 7 based on data corresponding to the standard tag and the private tag of past medical image data along the DICOM protocol acquired in a different version or grade of a MRI apparatus made by the same maker. Alternatively, the imaging condition setting unit 7 can automatically set imaging parameters, such as a matrix size, common to makers based on information corresponding to the standard tag of past medical image data along the DICOM protocol acquired by a MRI apparatus made by another maker.

However, imaging conditions included in past examination information acquired by the image diagnostic apparatus 1B made by another maker or a different type of the image diagnostic apparatus 1A made by the same maker may not be able to be set in the image diagnostic apparatus 1, similar to information designation imaging conditions included in examination order information. Then, the imaging condition setting unit 7 is configured to be able to set the imaging condition closest to an imaging condition included in past examination information automatically when the imaging condition included in the past examination information cannot be set. Consequently, even if a matrix size of medical image data which can be set as an imaging condition is different from a matrix size of past medical image data, the matrix size closest to the matrix size of the past medical image data can be set as an imaging condition, for example.

Note that, the imaging condition setting unit 7 may be configured to set imaging parameters as default values based on past examination information automatically so that the imaging parameters can be adjusted based on setting information from the input device 10. Alternatively, the imaging condition setting unit 7 may also be configured to automatically indicate an imaging condition based on past examination information to an operator through the display unit 11 so as to set an imaging condition when information confirming the indicated imaging condition is input to the imaging condition setting unit 7 from the input device 10.

In this case, the imaging condition setting unit 7 can also indicate plural candidates of imaging condition as choices based on examination information corresponding to plural past examinations so as to set an imaging condition for imaging according to information of selecting a choice input from the input device 10. Similarly, the imaging condition setting unit 7 may also indicate plural imaging conditions close to information designating imaging conditions included in examination order information, directed to the imaging diagnostic apparatus 1B made by another maker or a different type of the imaging diagnostic apparatus 1A made by the same maker, as choices to an operator when the imaging condition setting unit 7 has acquired the examination order information.

As described above, the imaging condition setting unit 7 is configured to be able to automatically set or indicate imaging conditions based on past examination information.

The imaging system 8 has a function to acquire medical image data of an object to be a patient by performing imaging according to imaging conditions set with referring the examination information by the imaging condition setting unit 7. Therefore, the imaging system 8 includes hardware to acquire imaging data from the object and a computer to generate medical image data by information processing of the acquired imaging data.

When the image diagnostic apparatus 1 is a MRI apparatus, the imaging system 8 includes hardware for acquiring NMR signals from an object, control equipments for controlling the hardware and a computer to generate MR image data by image reconstruction processing and image processing of acquired NMR signals. The hardware includes a magnet for a static magnetic field, gradient magnetic field coils and RF coils. The control equipments include a static magnetic supply, a gradient magnetic supply, a RF transmitter, a RF receiver, a sequence controller and a computer.

Alternatively, when the image diagnostic apparatus 1 is an X-ray CT apparatus, the imaging system 8 includes hardware such as an X-ray tube and an X-ray detector, control equipments such as a high-voltage generator, a driving system and a computer to control the hardware and a computer to generate X-ray CT image data by image reconstruction processing and image processing of detection signals by the X-ray detector.

The image data transmission unit 9 has a function to convert medical image data generated in the imaging system 8 to medical image data having a data structure along the DICOM protocol and transmit the medical image data along the DICOM protocol to a destination designated from the input device 10. The medical image data generated in the image diagnostic apparatus 1 is generally forwarded to the medical image server 4.

Next, operation and action of the image diagnostic apparatus 1 and the medical image server 4 will be described.

Figure 2:
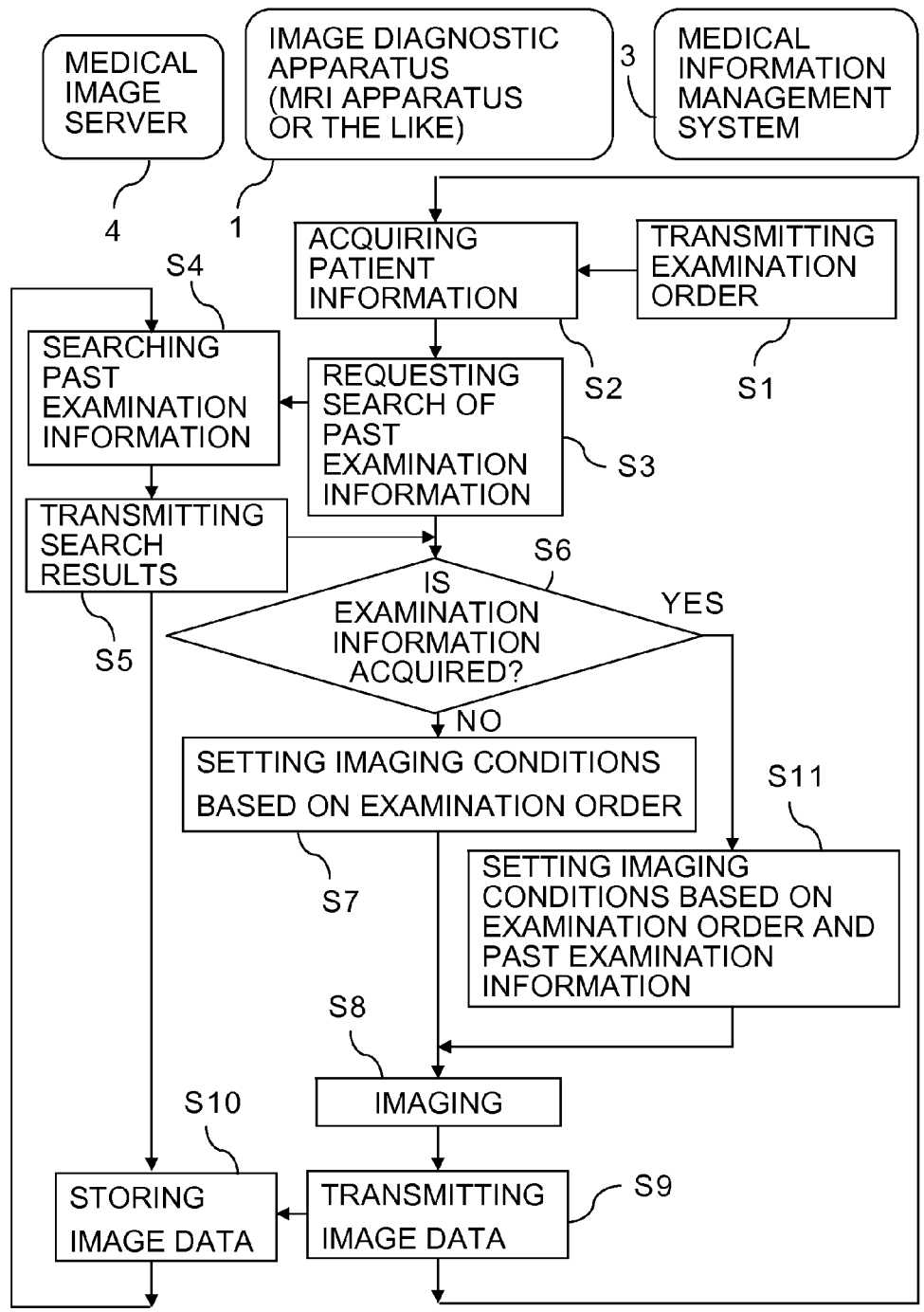
FIG. 2 is a sequence chart showing a flow for imaging with setting imaging conditions, by the image diagnostic apparatus shown in FIG. 1, based on examination information acquired from the medical image server.

FIG. 2 is a sequence chart showing a flow for imaging with setting imaging conditions, by the image diagnostic apparatus 1 shown in FIG. 1, based on examination information acquired from the medical image server 4.

Firstly, in step S1, examination order information is transmitted from the medical information management system 3 to the image diagnostic apparatus 1 through the network 2.

Next, in step S2, the patient information acquisition unit 5 of the image diagnostic apparatus 1 receives the examination order information and acquires patient information such as a patient ID included in the examination order information. The examination order information can be received from the image diagnostic apparatus 1 to be processed even if the examination order information corresponds to the imaging diagnostic apparatus 1B made by another maker or a different type of the image diagnostic apparatus 1A made by the same maker. Then, the patient information acquired by the patient information acquisition unit 5 is registered.

Next, in step S3, the examination information acquisition unit 6 transmits a request for transmitting past examination information corresponding to the patient information acquired by the patient information acquisition unit 5 and search conditions of the examination information to the medical image server 4 through the network 2 automatically. For example, the search conditions can be set as examination information corresponding to the same patient ID within 3 months.

Next, in step S4, the database control unit 4B of the medical image server 4 receives the request for transmitting examination information transmitted from the image diagnostic apparatus 1 through the network 2 and the search conditions to search the image database 4A according to the search conditions. When an examination of the patient identified by the patient ID is the first time, no past examination information corresponding to the search conditions is stored in the image database 4A. Therefore, the database control unit 4B determines no past examination information is stored in the image database 4A.

Next, in step S5, the database control unit 4B transmits determination of no past examination information as search results of examination information to the image diagnostic apparatus 1 through the network 2.

Next, in step S6, the examination information acquisition unit 6 of the image diagnostic apparatus 1 receives the search results of past examination information and determines whether the past examination information has been acquired or not. When the examination of the patient identified by the patient ID is the first time, the examination information acquisition unit 6 determines NO since the past examination information has not been acquired. Then, the examination information acquisition unit 6 notifies the determination result, that the past examination information has not been acquired, to the imaging condition setting unit 7.

In this case, in step S7, the imaging condition setting unite 7 sets imaging conditions based on the examination order information received by the patient information acquisition unit 5. When the image diagnostic apparatus 1 is a MRI apparatus, the imaging conditions setting unit 7 automatically sets imaging conditions for imaging based on information designating imaging conditions, such as an imaging part and types of reception coils, included in the examination order information.

Note that, the medical information management system 3 may supply examination order information, which is directed to the image diagnostic apparatus 1B made by another maker or a different type of the image diagnostic apparatus 1A made by the same maker, to the imaging condition setting unit 7. In this case, there is a possibility that information designating imaging conditions included in the examination order information cannot necessarily be set in the image diagnostic apparatus 1. Then, the imaging condition setting unit 7 automatically sets or indicates imaging conditions closest to the information designating imaging condition included in the examination order information. This enables to set imaging conditions corresponding to the examination order information regardless of whether the examination order information is directed to the same type of the image diagnostic apparatus made by the same maker or not.

Further, the input device 10 inputs information required for setting the other imaging conditions to the imaging condition setting unit 7. The imaging condition setting unit 7 sets the other imaging conditions based on the setting information of imaging conditions input from the input device 10.

Next, in step S8, the imaging system 8 performs imaging according to the imaging conditions set in the imaging condition setting unit 7. As a result, frames of medical image data of the object identified by the patient ID are acquired.

Next, in step S9, the image data transmission unit 9 converts the medical image data generated in the imaging system 8 into medical image data along the DICOM protocol and transmits the medical image data along the DICOM protocol to the medical image server 4 via the network 2.

Next, in step S10, the database control unit 4B of the medical image server 4 receives the medical image data along the DICOM protocol transmitted from the image diagnostic apparatus 1 via the network 2 and writes the medical image data along the DICOM protocol into the image database 4A as examination information corresponding to the patient ID.

Further, in a similar flow, medical image data acquired in an image diagnostic apparatus 1B made by another maker and/or another image diagnostic apparatus 1A made by the same maker can be written into the image database 4A. As a result, frames of medical image data corresponding to the patient ID are stored in the image database 4A.

Meanwhile, the image diagnostic apparatus 1 becomes a state waiting examination order information. Then, imaging and acquiring medical image data of various patients are performed repeatedly in a similar flow. Note that, when a reexamination of a same patient is performed, past medical image data corresponding to the patient ID, tag information attached to the past medical image data or information corresponding to the tag information having been attached to the past medical image data is acquired as examination information by the database control unit 4B in searching past examination information in step S4. In addition, medical image data and the like acquired from the same patient by an image diagnostic apparatus 1B made by another maker and/or another image diagnostic apparatus 1A made by the same maker are also acquired as past examination information by the database control unit 4B so long as search conditions are met.

In this case, in step S5, the database control unit 4B transmits the past examination information acquired as the search results to the image diagnostic apparatus 1 via the network 2. The past examination information is transmitted as image data along the DICOM protocol to the image diagnostic apparatus 1 when the past examination information is medical image data.

Therefore, in step S6, the examination information acquisition unit 6 of the image diagnostic apparatus 1 determines that the past examination information has been acquired. Subsequently, the examination information acquisition unit 6 supplies the past examination information acquired as the search results to the imaging condition setting unit 7.

In this case, in step S11, the imaging condition setting unit 7 sets imaging conditions based on both the examination order information and the past examination information received by the patient information acquisition unit 6. Note that, an operator may also confirm the imaging conditions indicated on the display unit 11 once by operating the input device 10, prior to setting the imaging conditions.

When the examination information acquisition unit 6 has been acquired past examination information as image data along the DICOM protocol acquired by the image diagnostic apparatus 1 or 1A made by the same maker, tag information attached to the image data along the DICOM protocol or information corresponding to the tag information having been attached to the image data along the DICOM protocol, information corresponding to a standard tag and a private tag is to be acquired as a part or all of the examination information. Accordingly, the imaging condition setting unit 7 automatically sets or indicates imaging parameters based on the information corresponding to the standard tag and the private tag.

On the contrary, when the examination information acquisition unit 6 has been acquired past examination information as image data along the DICOM protocol acquired by the image diagnostic apparatus 1B made by another maker, tag information attached to the image data along the DICOM protocol or information corresponding to the tag information having been attached to the image data along the DICOM protocol, information corresponding to a standard tag is to be acquired as a part or all of the examination information. Accordingly, the imaging condition setting unit 7 automatically sets or indicates imaging parameters based on the information corresponding to the standard tag.

When pieces of past examination information have been supplied to the imaging condition setting unit 7, the imaging condition setting unit 7 automatically selects past examination information to be appropriately referred to for setting imaging conditions base on the examination order information. Alternatively, the imaging condition setting unit 7 displays a list of pieces of past examination information on the display unit 11 and an operator manually selects past examination information to be appropriately referred to for setting imaging conditions by operating the input device 10.

For example, the latest medical image data acquired from an imaging part identified by information specifying the imaging part included in the examination order information, tag information attached to the latest medical image data or information corresponding to the tag information having been attached to the latest medical image data can be selected for setting imaging conditions. Then, the imaging condition setting unit 7 sets the imaging conditions based on the selected information and examination order information.

FIG. 3 is a view showing an example of setting screen for imaging conditions in MRI in case of setting the imaging conditions based on both examination order information and past examination information in the imaging condition setting unit 7 shown in FIG. 1.

As shown in FIG. 3, the imaging condition setting unit 7 can display a setting screen for imaging conditions, which displays examination order information and past examination information, on the display unit 11. Note that, FIG. 3 shows an example of allowing registration of patient information by the patient information acquisition unit 5 and registration of PAS information as an imaging condition on a common screen.

That is, examination order information including the patient information and information specifying an imaging part is displayed in a left area on the setting screen. When patient information including a patient ID is confirmed and the patient registration button is pressed by the input device 10, patient registration in the image diagnostic apparatus 1 can be performed.

On the other hand, past examination information acquired from the same imaging part and corresponding to the same patient ID is displayed in a right area on the setting screen. As the past examination information, imaging parameters including a TR and a TE can be also displayed in addition to a medical image and PAS information including a combination of imaging parameters used for acquiring the medical image. The past medical image can be acquired from the data area corresponding to the image tag of medical image data. PAS information and respective imaging parameters consisting of the PAS information can be acquired from the data areas corresponding to the standard tag and the private tag of medical image data.

Then, the imaging condition setting unit 7 automatically sets default values of PAS information as imaging conditions based on imaging conditions including the past examination information. When the past examination information has been acquired by the image diagnostic apparatus 1B made by another maker or a different type of the image diagnostic apparatus 1A made by the same maker and the imaging conditions included in the past examination information are not imaging conditions which can be set in the image diagnostic apparatus 1, the imaging condition setting unit 7 automatically sets imaging conditions closest to the imaging conditions included in the past examination information as default values.

Therefore, an operator can confirm the imaging parameters of the PAS information automatically set by the imaging condition setting unit 7 to correct the PAS information by inputting corrected information to the imaging condition setting unit 7 from the input device 10, as needed.

In addition, a region of interest (ROI) equivalent to a ROI set to acquire a past medical image can be set as an imaging condition for a reexamination by referring to the past medical image displayed on the setting screen for imaging conditions.

Then, the examination order information and the PAS information can be combined to be registered in the image diagnostic apparatus 1 by operating the input device 10 by an operator to press a PAS registration button. As a result, imaging condition, including a pulse sequence for imaging, similar to imaging conditions used for a past examination can be set.

That is, the image diagnostic apparatus 1 as described above is an apparatus which automatically searches past examination information in the medical image server 4 based on patient information included in examination order information so that the past examination information can be referred to for setting imaging conditions when the examination order information is supplied. On the other hand, the medical image server 4 is a system which searches past examination information according to a predetermined search conditions so that examination information acquired as search results can be supplied to the image diagnostic apparatus 1 in case of receiving a request for supplying past examination information corresponding to examination order information from the image diagnostic apparatus 1.

Therefore, the image diagnostic apparatus 1 and the medical image server 4 make it possible to omit searching works of past examination information so as to simplify a workflow in a reexamination with a modality such as a MRI. This makes it possible to reduce an examination time and a burden on a patient and an operator of the image diagnostic apparatus 1.

Especially, the image diagnostic apparatus 1 makes it possible to acquire and refer to a past medical image easily. Therefore, it becomes possible to set a ROI equivalent to that set for a past medical image as data acquisition positions. This makes it possible to perform an image comparative examination effectively.

In addition, the image diagnostic apparatus 1 can automatically set imaging parameters by referring to past examination information. Therefore, imaging conditions can be set easily without conventional cumbersome works that an operator reads out imaging conditions from a medical record out to input the imaging conditions. Especially, works to set imaging conditions can be simplified well in a MRI apparatus requiring a large number of imaging parameters.

Further, the imaging diagnostic apparatus 1 is an apparatus configured to automatically set imaging conditions closest to imaging conditions included in examination order information and/or imaging conditions corresponding to past examination information when examination order information generated for an image diagnostic apparatus 1B made by another maker or a different type of an imaging diagnostic apparatus 1A made by a same maker and/or past examination information acquired by an image diagnostic apparatus 1B made by another maker or a different type of an image diagnostic apparatus 1A made by a same maker is acquired.

Therefore, the image diagnostic apparatus 1 makes it possible to reduce dependence on experience and skills of an operator in work for setting imaging conditions.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

For example, in the embodiment described above, an example of automatically setting or indicating imaging conditions by referring to past examination information acquired with a same kind of image diagnostic apparatus (modality) has been described. However, imaging conditions may be set or indicated automatically by referring to past examination information acquired with a different kind of modality.

In this case, the examination information acquisition unit 6 is to acquire the past examination information as image data along the DICOM protocol acquired with a different kind of image diagnostic apparatus, tag information attached to the image data along the DICOM protocol or information corresponding to the tag information having been attached to the image data along the DICOM protocol. Therefore, information corresponding to the standard tag of the image data along the DICOM protocol is acquired as a part or all of the past examination information. Then, the imaging condition setting unit 7 can automatically set or indicate imaging parameters based on at least the information corresponding to the standard tag.

As a concrete example, when imaging with a PET apparatus and imaging with a MRI apparatus are performed to an almost same imaging part of a same object, imaging parameters of one apparatus such as data acquisition positions, a size of image and a resolution can be applied with those of the other. In this case, information corresponding to the standard tag of image data acquired with one of the PET apparatus and the MRI apparatus is acquired as a part or all of examination information by the examination information acquisition unit 6. Then, the imaging condition setting unit 7 sets or indicates imaging parameters of the other automatically.

What is claimed is:

1. A diagnostic imaging apparatus comprising:
a medical imager configured to transmit energy in the form of electromagnetic waves or ultrasonic vibrations into a patient anatomy and, based on a sensed response, to generate a diagnostic image of the patient anatomy, the medical imager performing its operations based on set imaging conditions and including at least one processor and associated memory configured by computer programs and/or hardware to
search a network-connected medical image server, based on patient information, to automatically acquire past examination information corresponding to the patient information from the medical image server when the patient information is supplied to said medical imager, wherein the past examination information corresponds to at least one of (a) a diagnostic imaging apparatus made by a different maker, (b) a diagnostic imaging apparatus made by a same maker and (c) a different kind of diagnostic imaging apparatus, each of said diagnostic imaging apparatuses having acquired, a medical image based on a sensed response from transmission of energy in the form of electromagnetic waves or ultrasonic vibration into patient anatomy; and
perform imaging according to an imaging condition set by referring to the automatically acquired past examination information.

2. The diagnostic imaging apparatus of claim 1, wherein:
the imaging condition is automatically set based on the automatically acquired past examination information.

3. The diagnostic imaging apparatus of claim 2, wherein:
an imaging parameter is automatically set or indicated based on information corresponding to a standard tag of image data acquired by a diagnostic imaging apparatus made by a different maker when the information corresponding to the standard tag was acquired as a part or all of the examination information, the image data conforming to a DICOM (Digital Imaging and COmmunication in Medicine) protocol.

4. The diagnostic imaging apparatus of claim 3, wherein said medical imager is configured to acquire tag information as a part or all of the examination information, the tag information being attached to image data.

5. The diagnostic imaging apparatus of claim 3, wherein said medical imager is configured to acquire information corresponding to tag information as a part or all of the examination information, the tag information having been attached to image data.

6. The diagnostic imaging apparatus of claim 2, wherein:
an imaging parameter is automatically set or indicated based on information corresponding to a standard tag and a private tag of image data acquired by an image diagnostic apparatus made by a same maker when the information corresponding to the standard tag and the private tag was acquired as a part or all of the examination information, the image data conforming to a DICOM (Digital Imaging and COmmunication in Medicine) protocol.

7. An image diagnostic apparatus of claim 2, wherein:
an imaging parameter is automatically set or indicated based on at least information corresponding to a standard of image data acquired by a different kind of an image diagnostic apparatus tag when the information corresponding to the standard tag was acquired as a part or all of the past examination information, the image data conforming to a DICOM (Digital Imaging and COmmunication in Medicine) protocol.

8. The diagnostic imaging apparatus of claim 7, wherein:
an imaging parameter of one of (i) a positron emission computed tomography (PET) apparatus and (ii) a magnetic resonance imaging (MRI) apparatus is automatically set or indicated when information corresponding to a standard tag of image data acquired by another positron emission computed tomography apparatus and/or magnetic resonance imaging apparatus was acquired as part or all of the past examination information.

9. The diagnostic imaging apparatus as in claim 1 wherein:
an imaging condition closest to information designating an imaging condition included in examination order information directed to (i) a diagnostic imaging apparatus made by another maker or (ii) a different type of diagnostic imaging apparatus made by a same maker is automatically set or indicated when the examination order information is supplied from a network-connected medical information management system; and
said imaging is performed according to the set or indicated imaging condition.

10. The diagnostic imaging apparatus of claim 9, wherein:
said imaging condition setting unit is configured to set or indicate a pulse sequence for magnetic resonance imaging as the imaging is set or indicated condition.

11. The diagnostic imaging apparatus of claim 1, wherein
an imaging condition closest to information designating an imaging condition included in the automatically acquired past examination information is set or indicated.

12. A medical image server comprising:
at least one processor and associated memory;
a database memory configured to store medical image data acquired based on a sensed response from transmission of energy in the form of electromagnetic waves or ultrasonic vibrations into patient anatomy and including past patient information and past examination information associated therewith; and
wherein said processor and associated memory has been configured to search the database, based on patient information managed in a network-connected medical information management system, to acquire past examination information corresponding to the patient information and to transmit the acquired past examination information to a network-connected diagnostic imaging apparatus when a request for transmitting the past examination information corresponding to the patient information is transmitted from the network-connected diagnostic imaging apparatus wherein the past examination information corresponds to at least one of (a) a diagnostic imaging apparatus made by a different maker, (b) a diagnostic imaging apparatus made by a same maker and a different kind of diagnostic imaging apparatus, each of said diagnostic imaging apparatuses having acquired a medical image based on a sensed response from transmission of energy in the form of electromagnetic waves or ultrasonic vibration into patient anatomy.

13. A diagnostic imaging method comprising:
using a medical imager configured to transmit energy in the form of electromagnetic waves or ultrasonic vibrations into a patient anatomy and, based on a sensed response, to generate a diagnostic image of the patient anatomy, the medical imager performing its operations based on set imaging conditions and including at least one processor and associated memory configured by computer programs and/or hardware by
searching a network-connected medical image server based on input patient information to automatically acquire past examination information corresponding to the patient information from the medical image server when the patient information is supplied from a network-connected medical information management system wherein the past examination information corresponds to at least one of (a) a diagnostic imaging apparatus made by a different maker, (b) a diagnostic imaging apparatus made by a same maker and (c) a different kind of diagnostic imaging apparatus, each of said diagnostic imaging apparatuses having acquired, a medical image based on a sensed response from transmission of energy in the form of electromagnetic waves or ultrasonic vibration into patient anatomy; and
performing diagnostic imaging according to an imaging condition set by referring to the automatically acquired past examination information.

14. A diagnostic imaging method comprising:
using a medical imager configured to transmit energy in the form of electromagnetic waves or ultrasonic vibrations into a patient anatomy and, based on a sensed response, to generate a diagnostic image of the patient anatomy, the medical imager performing its operations based on set imaging conditions and including at least one processor and associated memory configured by computer programs and/or hardware by
automatically setting or indicating an imaging condition closest to information designating an imaging condition included in examination order information directed over a network connection to an image diagnostic apparatus made by a different or a different type of an image diagnostic apparatus made by a same maker when the examination order information is supplied from a network connected medical information management system, wherein the past examination information corresponds to at least one of (a) a diagnostic imaging apparatus made by a different maker, (b) a diagnostic imaging apparatus made by a same maker and (c) a different kind of diagnostic imaging apparatus, each of said diagnostic imaging apparatuses having acquired, a medical image based on a sensed response from transmission of energy in the form of electromagnetic waves or ultrasonic vibration into patient anatomy; and
performing diagnostic imaging according to the set or indicated imaging condition.

* * * * *